United States Patent

Holtzclaw et al.

Patent Number: 4,780,282
Date of Patent: Oct. 25, 1988

[54] DOSIMETER FOR MEASURING EXPOSURE TO HYDRAZINE AND HAZARDOUS HYDRAZINE DERIVATIVES

[75] Inventors: James R. Holtzclaw, Palm Harbor, Fla.; Susan L. Rose, Alexandria; Jeffrey R. Wyatt, Burke, both of Va.; Chester M. Hawkins, Trappe, Md.

[73] Assignees: Geo-Centers, Inc., Newton Centre, Mass.; United States of America, Washington, D.C.

[21] Appl. No.: 905,683

[22] Filed: Sep. 9, 1986

[51] Int. Cl.⁴ ............... G01N 31/22; G01N 33/22
[52] U.S. Cl. ............................. 422/56; 422/58; 422/88; 436/106; 436/902
[58] Field of Search ............ 422/88, 94; 436/106, 436/902; 422/56, 58

[56] References Cited

U.S. PATENT DOCUMENTS 3,455,656  7/1969  Roberts et al. ............ 436/106 X
3,985,017 10/1976  Goldsmith ................. 422/83 X
4,256,694  3/1981  McAllister et al. ........ 422/86 X

FOREIGN PATENT DOCUMENTS 859919  8/1981  U.S.S.R. .................. 436/106
864074  9/1981  U.S.S.R. .................. 436/106

OTHER PUBLICATIONS

Leichnitz, *Detector Tube Handbook*, Dräger, Lübeck, Germany (1979) 4th Ed., p. 84.

Primary Examiner—Barry S. Richman
Assistant Examiner—Jill Johnston
Attorney, Agent, or Firm—Wolf, Greenfield & Sacks

[57] ABSTRACT

A dosimeter for collecting vapors and gases of hydrazine and of hazardous derivatives of hydrazine such as monomethylhydrazine and 1,1-dimethylhydrazine, employs a housing with a perforated cover. Situated inside the housing is a removable disk on which is coated a solution of citric acid in methanol. The solution initially contains 20% to 30% of citric acid monohydrate dissolved in methanol and the solution is permitted to age for seven or eight days before being coated on to the disk.

3 Claims, 1 Drawing Sheet

4,780,282

DOSIMETER FOR MEASURING EXPOSURE TO HYDRAZINE AND HAZARDOUS HYDRAZINE DERIVATIVES

U.S. GOVERNMENT RIGHTS IN THE INVENTIION

This invention was made jointly by employees of the Naval Research Laboratory and an employee of Geo-Centers, Inc., who was in the performance of work under Naval Research Laboratory contract N00014-84-C-2011. The United States of America has certain rights in the invention arising out of that contract, including a nonexclusive, nontransferable irrevocable, paid-up license to practice the invention or have it practiced for or on behalf of the United States throughout the world.

FIELD OF THE INVENTION

This invention relates in general to safety devices for detecting gases and vapors of hazardous materials. More particularly, the invention pertains to a passive device for monitoring the exposure of a person to vapors of hydrazine and hazardous derivatives of hydrazine, such as monomethylhydrazine and 1,1-dimethylhydrazine.

BACKGROUND OF THE INVENTION

Hydrazine is a colorless liquid, $H_2NNH_2$, with a fish-like odor and a boiling point of 114° C. Major uses of hydrazine include its employment for rocket fuels, as a corrosion inhibitor in boilers, and for the synthesis of biologically active materials such as plant-growth regulators. Exposure to vapors of hydrazine or vapors of a hydrazine derivative such as monomethylhydrazine is harmful to the human body. Even small concentrations of liquid hydrazine or certain hazardous derivatives of hydrazine can be harmful because of the ability of those substances to enter the body through the skin and attack internal organs. Vapors of those substances, even in low concentrations, are suspected of being carcinogenic. Consequently, in an environment where some persons may be exposed to the harmful vapors for different periods of time and to different vapor concentrations, there is a need for an inexpensive device for measuring each person's exposure to such vapors.

Few acceptable techniques are known for measuring a person's exposure to hydrazine or to hazardous derivatives of hydrazine. Of the few techniques that are now available, those that rely upon substances which change color when exposed to hydrazine lack the necessary sensitivity to low concentrations of hydrazine or its hazardous derivatives and most of the other techniques are either too cumbersome for use in personal monitoring or are not sufficiently reliable to enable a dependable evaluation of exposure to be made.

OBJECT OF THE INVENTION

Hydrazine, monomethylhydrazine, and 1,1-dimethyl hydrazine are volatile compounds that tend to decompose when exposed to the atmosphere. It is an object of the invention to provide a portable dosimeter for collecting hydrazine and those hydrazine derivatives and keeping those collected substances in their stable states until the collections can be analyzed to ascertain the amounts collected.

THE INVENTION

The invention arises out of the observation that a weak acid inhibits the decomposition of hydrazine, monomethylhydrazine, and 1,1-dimethylhydrazine when those substances are exposed to the atmosphere. It has been determined that hydrazine and monomethylhydrazine remain stable for periods of at least 8 days after vapors of those substances are deposited upon a substrate coated with a solution of citric acid in methanol. The invention resides in a badge having an arrangement for collecting vapors and gases of hydrazine, monomethylhydrazine, and 1,1-dimethylhydrazine on a removable disk coated with a solution of citric acid in methanol.

THE DRAWINGS

DETAILED DESCRIPTION OF THE PREFERRED EMBODIMENT

Figure 1:
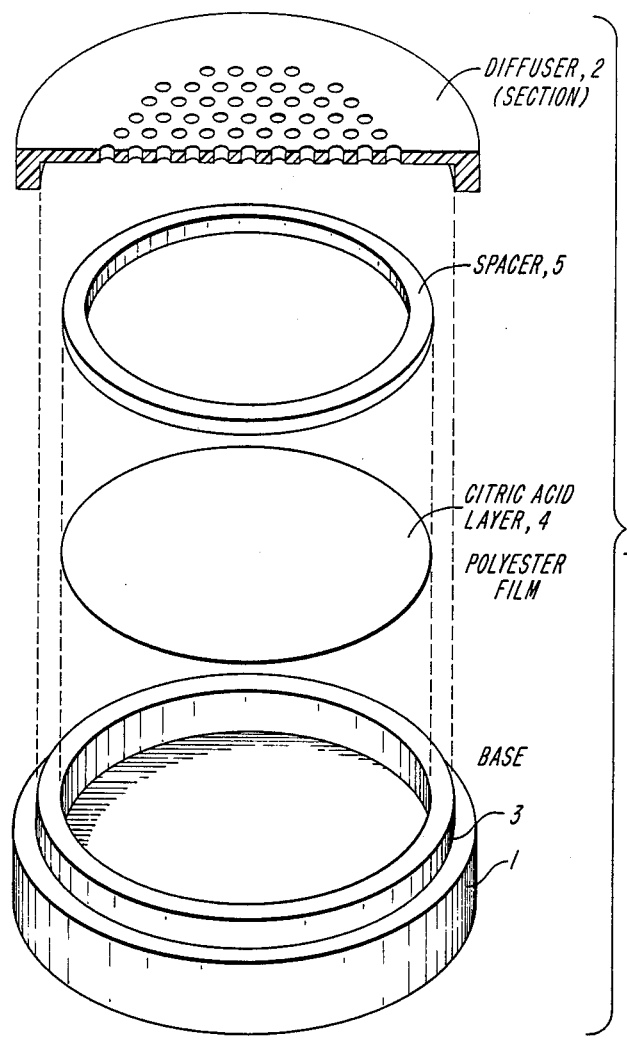
FIG. 1 is an exploded perspective view showing the preferred embodiment of the invention.
Figure 2:
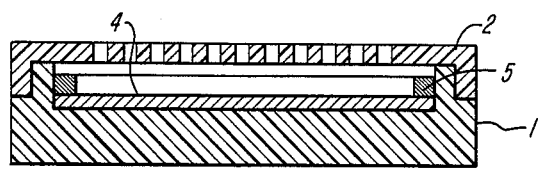
FIG. 2 is a cross-sectional view in elevation of the preferred embodiment.

Referring now to the exploded view of the invention depicted in FIG. 1 and to the cross-sectional view in FIG. 2, the preferred embodiment of the invention is in the form of a badge to be worn on the outer clothing of the person to be monitored for exposure to the vapors of hydrazine and derivatives of hydrazine. The badge has a housing formed by a hollow cylindrical base 1 and a perforated cover 2. The base and cover are molded of a chemically inert material such as Teflon, that is minimally affected by hydrazine or by monomethylhydrazine, or by 1,1-dimethylhydrazine. The cylindrical base 1 has a shallow chamber that is, for example, about 3/32" deep with an internal diameter of about 1½". The cover 2 preferably provides an air tight closure around the base and because of that tight fit, the cover cannot be easily separated from the base. To aid in the formation of an air tight seal, the cover rests on a ledge 3 on the base. Where desired, the cover can be secured to the base by a bayonet mount, by screw threads, or by other attachment means and the ledge can be eliminated.

Disposed within the housing is a disk 4 of Mylar drafting film (or of a polyester film having similar characteristics) which was dipped in a solution of citric acid in methanol. Preferably the citric acid-methanol solution was permitted to age for at least seven or eight days before being used. It has been found from experience that the citric acid is less apt to crystalize on the disk when the solution has been aged. The solution is prepared by mixing 20% to 30% of citric acid monohydrate with methanol. It is believed that a percentage of those constituents react to form methyl citrate although an experiment made to test that belief proved to be inconclusive. However, the improvement obtained with aging of the solution and the tendency of the solution when aged too long to rapidly dry out when deposited on the Mylar film, lends support to the belief that a slow reaction has occurred. It is likely that an unknown but certain percentage of methyl citrate must be formed in the solution to obtain optimal performance of the badge. If such a reaction is a necessary condition, then it is probable that a solution of methyl citrate can be applied to the Mylar disk in place of the citric acid-methanol solution.

Citric acid is commercially available in anhydrous form, in monohydrate form, and in other hydrated forms. No reason is apparent why those forms of citric acid cannot be used interchangably with equal or similar results. Commercial polyester drafting films, such as that sold under the Mylar trademark, have a matte surface on one side with the opposite side usually being glossy. When that kind of drafting film is used, the glossy side of the disk is washed to remove the citric acid-methanol coating and the coating on the matte surface is allowed to dry for five or ten minutes before the disk is placed in the housing. The coated surface remains tacky—that is, remains somewhat sticky to the touch. The disk, with the tacky surface uppermost, is placed on the floor of the base and is held in place by a retaining ring 5 which is pressed into the shallow chamber of the base. In lieu of using a press fit, other retaining means, such as screw threads may be provided.

After the coated film and retaining ring have been inserted into the base, the housing is closed by seating the cover 2 on the ledge 3 of the base. There is then a space of about 3/32" between the cover and the coated disk. The cover 2, for example, has 140 holes of 1 mm. diameter in it which are evenly distributed within a 1" diameter circle. The holes are for diffusion control and aid in reducing air velocity effects where the hydrazine vapors or monomethylhydrazine vapors are air borne with air velocities in the range normally encountered in workplace environments. To promote diffusion control, it is desirable to minimize seepage around the cover.

The hydrazine deposited on the disk tends to be stabilized by the citric acid-methanol coating—that is, decomposition of the hydrazine is inhibited by the film of citric acid-methanol solution on the disk. Monomethylhydrazine and 1,1-dimethylhydrazine which are somewhat less stable than hydrazine are also stabilized by the coating.

It has been determined that badges can be stored for up to 8 days after exposure with no discernable loss of collected hydrazine or monomethylhydrazine. Badges have been exposed for periods of time up to 4 days and the results have remained linear except where the vapor concentration and/or exposure time has approached zero. Ammonia, freons, and isopropyl alcohol interfere minimally with sampling by the badge. There are virtually no humidity effects associated with the citric acid coating itself. However, the badge itself does have some small humidity effects, especially at low dosages. The humidity effects are minimized by molding the Teflon casing rather than machining it.

To determine the amount of hydrazine and hydrazine derivatives that have been collected, the badge is disassembled to remove the coated disk. The citric acid coat with its collected hydrazine and hydrazine derivatives is removed from the Mylar disk. The citric acid coat can, for example, be washed off the disk with dilute sulfuric acid. A strong acid, such as concentrated mineral acids, should not be used as it tends to destabilize the collected hydrazine and hydrazine derivatives. Wet chemical or other methods can then be used to ascertain the hydrazine and the hydrazine derivative content. Monomethylhydrazine can be analyzed, for example, using phosphomolybdic acid in NIOSH approved method #S149. Alternatively, monomethylhydrazine can be analyzed by coulometric titration with bromide and amperometric detection of the endpoint. The methods of analysis form no part of this invention and any suitable analytic method may be employed to ascertain the amount of collected hydrazine or the amount of collected hydrazine derivatives.

Although the invention has been described in the preferred embodiment of a badge to monitor the exposure of the bearer to hydrazine and its hazardous derivatives, the invention can be embodied in forms other than as a badge. For example the invention can be placed at fixed sites to monitor the presence of hydrazine vapors or vapors of its hazardous derivatives at locations where spillage of the material or release of the vapors is likely to occur. In circumstances where the invention is to be employed at fixed sites, the coated film can be held in an immovable casing of suitable configuration.

We claim:

1. In a dosimeter for collecting vapors and gases of hydrazine and hazardous hydrazine derivatives, where the dosimeter comprises
    a case with a shallow cavity therein, the case having a perforate cover in which there are a plurality of holes providing entry for the vapors and gases into the shallow cavity,
  the improvement comprising
    a removable substrate disposed in the shallow cavity in a manner providing a space in the cavity between the cover and a surface of the substrate, and
    a coating of a solution of citric acid in methanol disposed on said surface of the substrate.

2. The improvement according to claim 1, wherein the substrate is a polyester sheet.

3. The improvement according to claim 1, wherein the coating initially contains citric acid or a hydrate thereof dissolved in methanol.

* * * * *